US012727849B2

(12) United States Patent
Katsuyama

(10) Patent No.: US 12,727,849 B2
(45) **Date of Patent: *Sep. 8, 2026**

(54) CONTROL METHOD OF AN ULTRASONIC DIAGNOSTIC APPARATUS AND NON-TRANSITORY COMPUTER READABLE RECORDING MEDIUM

(71) Applicant: FUJIFILM Corporation, Tokyo (JP)

(72) Inventor: Kimito Katsuyama, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 71 days.

This patent is subject to a terminal disclaimer.

(21) Appl. No.: 18/965,809

(22) Filed: Dec. 2, 2024

(65) Prior Publication Data

US 2025/0090134 A1 Mar. 20, 2025

Related U.S. Application Data

(60) Continuation of application No. 17/681,492, filed on Feb. 25, 2022, now Pat. No. 12,186,126, which is a (Continued)

(30) Foreign Application Priority Data

Aug. 30, 2013 (JP) ................................ 2013-179830

(51) Int. Cl.
*A61B 8/08* (2006.01)
*A61B 8/00* (2006.01)
(Continued)

(52) U.S. Cl.
CPC ............ *A61B 8/0841* (2013.01); *A61B 8/145* (2013.01); *A61B 8/4488* (2013.01); *A61B 8/461* (2013.01);
(Continued)

(58) Field of Classification Search
CPC ................ A61B 8/5207; A61B 8/0841; A61B 2090/378; A61B 2017/3413; A61B 2090/3925
See application file for complete search history.

(56) References Cited

U.S. PATENT DOCUMENTS 6,048,312 A * 4/2000 Ishrak ................. A61B 8/0833 600/443
9,642,592 B2 * 5/2017 Wang .................. A61B 8/5246
(Continued)

FOREIGN PATENT DOCUMENTS

JP 2004208859 A * 7/2004
JP 2006346477 A * 12/2006
(Continued)

OTHER PUBLICATIONS

Advisory Action issued in co-pending U.S. Appl. No. 15/055,143, filed Feb. 14, 2019.

(Continued)

*Primary Examiner* — Keith M Raymond
*Assistant Examiner* — Johnathan Maynard
(74) *Attorney, Agent, or Firm* — Birch, Stewart, Kolasch & Birch, LLP

(57) ABSTRACT

A needle direction estimation unit estimates a needle direction L based on needle information generated by a needle information generation unit, and outputs the position information of the needle direction L. A search region setting unit sets the needle direction L in a tissue image based on the position information of the needle direction L, and sets a search region F that extends to both sides with a predetermined width r. A needle tip search unit calculates the brightness distribution of the tissue image, determines a maximum brightness point B in the search region F to be the needle tip, and outputs the position information of the needle tip. A needle tip visualizing unit visualizes a needle tip N,
(Continued)

which is a predetermined point image, in the tissue image from the position information of the needle tip.

16 Claims, 10 Drawing Sheets

Related U.S. Application Data division of application No. 15/055,143, filed on Feb. 26, 2016, now abandoned, which is a continuation of application No. PCT/JP2014/062064, filed on May 1, 2014.

(51) Int. Cl.

| | |
|---|---|
| ***A61B 8/14*** | (2006.01) |
| ***A61B 17/34*** | (2006.01) |
| ***A61B 90/00*** | (2016.01) |
| ***A61M 25/01*** | (2006.01) |
| ***G01S 7/52*** | (2006.01) |
| ***G01S 15/89*** | (2006.01) |

(52) U.S. Cl.

CPC .......... *A61B 8/5207* (2013.01); *A61B 8/5223* (2013.01); *G01S 7/52036* (2013.01); *G01S 15/8915* (2013.01); *A61B 8/466* (2013.01); *A61B 2017/3413* (2013.01); *A61B 2090/378* (2016.02); *A61M 25/0105* (2013.01)

(56) References Cited

U.S. PATENT DOCUMENTS

| | | | | |
|---|---|---|---|---|
| 2004/0002653 | A1* | 1/2004 | Greppi | A61B 8/483 600/431 |
| 2007/0270687 | A1* | 11/2007 | Gardi | G06T 7/254 600/425 |
| 2010/0056917 | A1* | 3/2010 | Karasawa | A61B 8/0841 600/443 |
| 2010/0160783 | A1* | 6/2010 | Halmann | A61B 8/4281 600/447 |
| 2010/0204579 | A1 | 8/2010 | Yoshida et al. | |
| 2010/0298705 | A1* | 11/2010 | Pelissier | A61B 8/4254 600/443 |
| 2011/0282209 | A1 | 11/2011 | Miyaki et al. | |
| 2012/0078103 | A1* | 3/2012 | Tashiro | A61B 8/461 600/443 |
| 2012/0253181 | A1* | 10/2012 | Okamura | A61B 8/5238 600/424 |
| 2014/0031673 | A1* | 1/2014 | Amemiya | A61B 8/0841 600/459 |
| 2014/0187942 | A1 | 7/2014 | Wang et al. | |
| 2016/0174932 | A1 | 6/2016 | Katsuyama | |
| 2016/0199023 | A1* | 7/2016 | Pelissier | G06T 7/0016 600/424 |

FOREIGN PATENT DOCUMENTS

| | | | |
|---|---|---|---|
| JP | 2010-183935 | A | 8/2010 |
| JP | 2012-70837 | A | 4/2012 |
| JP | 2012-120747 | A | 6/2012 |
| JP | 2012-213606 | A | 11/2012 |
| WO | WO 2011/058840 | A1 | 5/2011 |

OTHER PUBLICATIONS

Advisory Action issued in co-pending U.S. Appl. No. 15/055,143, filed Feb. 25, 2021.

Advisory Action issued in co-pending U.S. Appl. No. 15/055,143, filed Feb. 3, 2022.

Advisory Action issued in co-pending U.S. Appl. No. 15/055,143, filed Jul. 22, 2024.

Advisory Action issued in co-pending U.S. Appl. No. 17/681,492, filed Jul. 22, 2024.

Examiner's Answer issued in co-pending U.S. Appl. No. 15/055,143, filed Aug. 11, 2022.

Final Office Action issued in co-pending U.S. Appl. No. 15/055,143, filed Aug. 25, 2021.

Final Office Action issued in co-pending U.S. Appl. No. 15/055,143, filed Feb. 2, 2024.

Final Office Action issued in co-pending U.S. Appl. No. 15/055,143, filed Nov. 19, 2020.

Final Office Action issued in co-pending U.S. Appl. No. 15/055,143, filed Oct. 16, 2019.

Final Office Action issued in co-pending U.S. Appl. No. 15/055,143, filed Oct. 19, 2018.

Final Office Action issued in co-pending U.S. Appl. No. 17/681,492, filed Feb. 15, 2024.

International Preliminary Report on Patentability and English translation of the Written Opinion of the International Searching Authority (Forms PCT/IB/338, PCT/IB/373 and PCT/ISA/237), dated Mar. 10, 2016, for International Application No. PCT/JP2014/062064.

International Search Report for PCT/JP2014/062064 (PCT/ISA/210) mailed on Jun. 17, 2014.

Japanese Office Action, issued Sep. 6, 2016, for Japanese Application No. 2014-177374, along with an English machine translation.

Non-Final Office Action issued in co-pending U.S. Appl. No. 15/055,143, filed Apr. 5, 2019.

Non-Final Office Action issued in co-pending U.S. Appl. No. 15/055,143, filed Jul. 28, 2023.

Non-Final Office Action issued in co-pending U.S. Appl. No. 15/055,143, filed Mar. 28, 2018.

Non-Final Office Action issued in co-pending U.S. Appl. No. 15/055,143, filed Mar. 31, 2021.

Non-Final Office Action issued in co-pending U.S. Appl. No. 15/055,143, filed May 12, 2020.

Non-Final Office Action issued in co-pending U.S. Appl. No. 17/681,492, filed Aug. 7, 2023.

Non-Final Office Action issued in co-pending U.S. Appl. No. 17/681,492, filed Dec. 28, 2022.

Notice of Allowance issued in co-pending U.S. Appl. No. 17/681,492, filed Sep. 13, 2024.

Oral Hearing Transcript issued in co-pending U.S. Appl. No. 15/055,143, filed May 12, 2023.

Patent Board Decision issued in co-pending U.S. Appl. No. 15/055,143, filed Apr. 7, 2023.

* cited by examiner

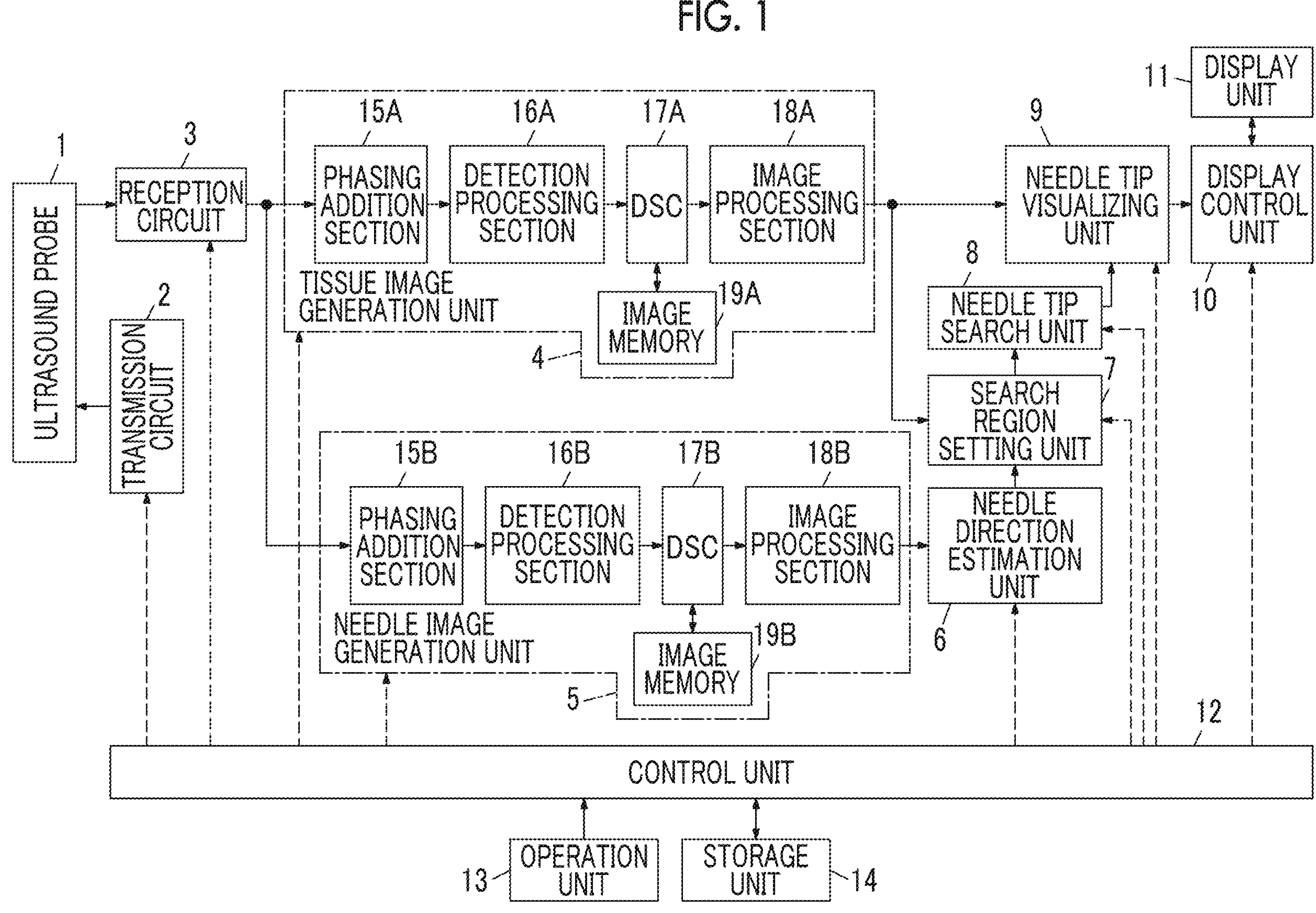
FIG. 1
ULTRASOUND PROBE
1
TRANSMISSION CIRCUIT
2
RECEPTION CIRCUIT
3
15A
PHASING ADDITION SECTION
16A
DETECTION PROCESSING SECTION
17A
DSC
18A
IMAGE PROCESSING SECTION
TISSUE IMAGE GENERATION UNIT
IMAGE MEMORY
19A
4
15B
PHASING ADDITION SECTION
16B
DETECTION PROCESSING SECTION
17B
DSC
18B
IMAGE PROCESSING SECTION
NEEDLE IMAGE GENERATION UNIT
IMAGE MEMORY
19B
5
9
NEEDLE TIP VISUALIZING UNIT
8
NEEDLE TIP SEARCH UNIT
7
SEARCH REGION SETTING UNIT
NEEDLE DIRECTION ESTIMATION UNIT
6
11
DISPLAY UNIT
DISPLAY CONTROL UNIT
10
12
CONTROL UNIT
13
OPERATION UNIT
STORAGE UNIT
14

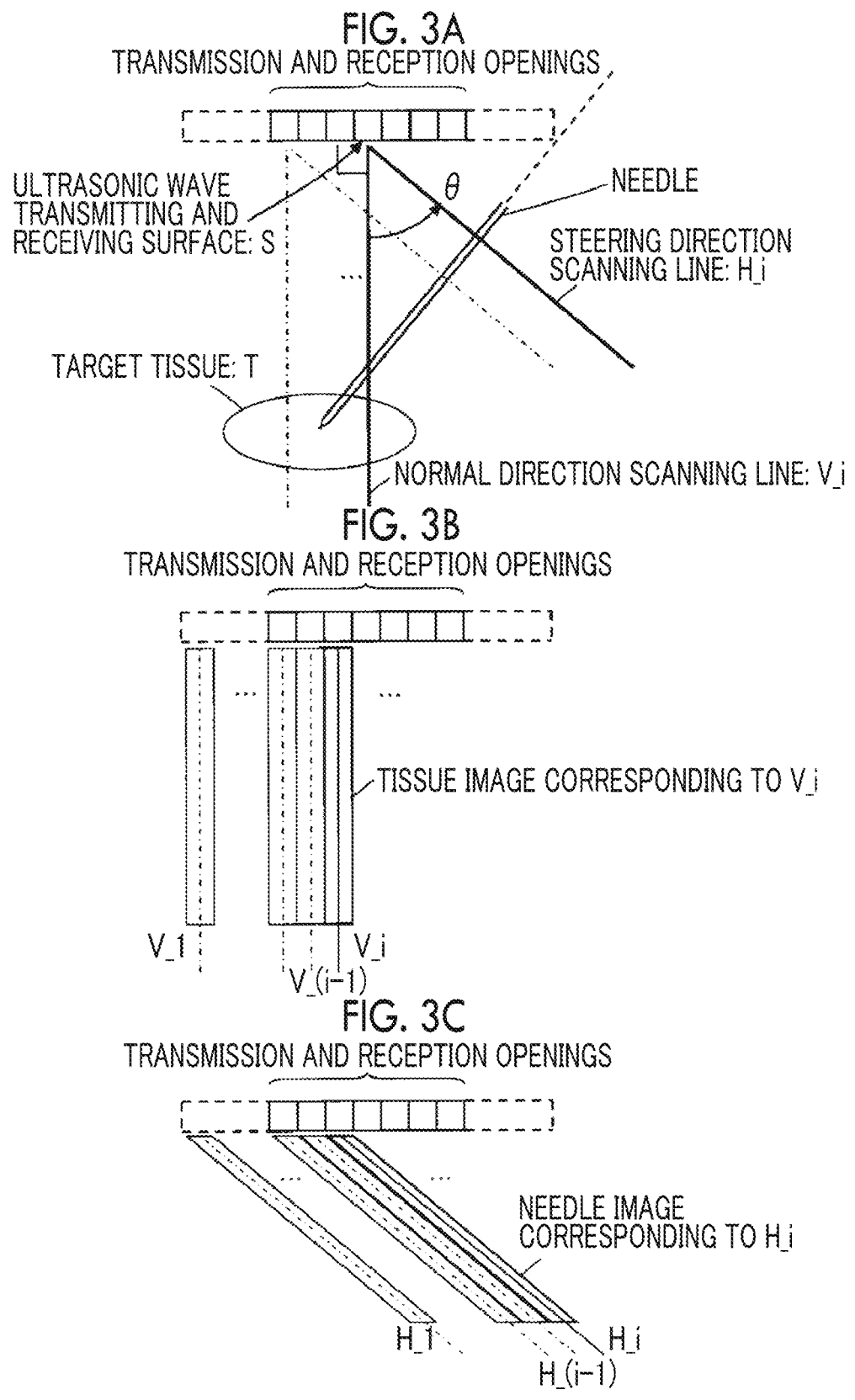

TRANSMISSION AND RECEPTION OPENINGS

ULTRASONIC WAVE TRANSMITTING AND RECEIVING SURFACE: S

θ

NEEDLE

STEERING DIRECTION SCANNING LINE: H_i

...

TARGET TISSUE: T

NORMAL DIRECTION SCANNING LINE: V_i

FIG. 3B

TRANSMISSION AND RECEPTION OPENINGS

...

...

TISSUE IMAGE CORRESPONDING TO V_i

TRANSMISSION AND RECEPTION OPENINGS

...

...

NEEDLE IMAGE CORRESPONDING TO H_i

NEEDLE DIRECTION: L

FIG. 5

NEEDLE DIRECTION: L
SEARCH REGION: F
REGION: W
PREDETERMINED WIDTH: r

FIG. 6

SEARCH REGION: F

NEEDLE DIRECTION: L

MAXIMUM BRIGHTNESS POINT: B

REGION: W

FIG. 7

NEEDLE

NEEDLE TIP: N

REGION: W

FIG. 8

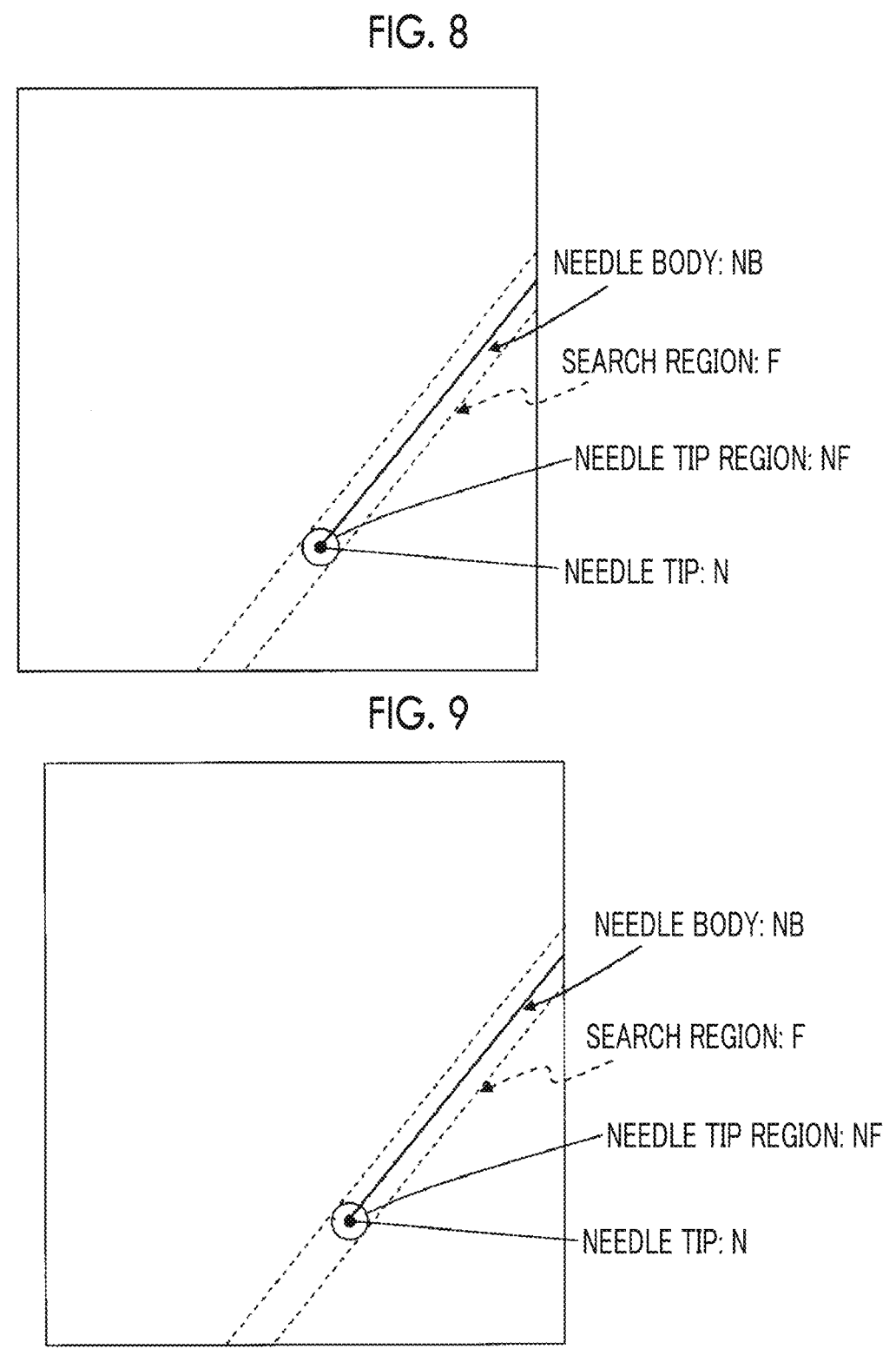

NEEDLE BODY: NB
SEARCH REGION: F
NEEDLE TIP REGION: NF
NEEDLE TIP: N

FIG. 9

NEEDLE BODY: NB
SEARCH REGION: F
NEEDLE TIP REGION: NF
NEEDLE TIP: N

NEEDLE BODY: NB

SEARCH REGION: F

NEEDLE TIP REGION: NF

NEEDLE TIP: N

...

NEEDLE TIP PATTERN
HIGH-BRIGHTNESS POINT
NEEDLE
HIGH-BRIGHTNESS POINT

SEARCH REGION: F
NEEDLE
NEEDLE DIRECTION: L
PREDETERMINED LENGTH: d
HIGH-BRIGHTNESS POINT: B1
HIGH-BRIGHTNESS POINT: B2

SEARCH REGION: F
NEEDLE DIRECTION: L
NEEDLE
P1
REGION: W

CONTROL METHOD OF AN ULTRASONIC DIAGNOSTIC APPARATUS AND NON-TRANSITORY COMPUTER READABLE RECORDING MEDIUM

CROSS REFERENCE TO RELATED APPLICATIONS

This application is a continuation of co-pending U.S. patent application Ser. No. 17/681,492, filed Feb. 25, 2022, which is a divisional application of co-pending U.S. patent application Ser. No. 15/055,143, filed Feb. 26, 2016, which is a continuation application of International Application PCT/JP2014/062064 filed on May 1, 2014, which claims priority under 35 U.S.C. 119 (a) to Application No. 2013-179830 filed in Japan on Aug. 30, 2013 all of which are hereby expressly incorporated by reference, in their entirety, into the present application.

BACKGROUND OF THE INVENTION

1. Field of the Invention

The present invention relates to an ultrasonic diagnostic device and an ultrasonic image generation method, and in particular, to an ultrasonic diagnostic device that visualizes the positional relationship between the needle direction and the target tissue and the positional relationship between the needle tip and the target tissue by visualizing the needle tip of the needle inserted into the subject in an ultrasonic image.

2. Description of the Related Art

Conventionally, in the medical field, an ultrasonic diagnostic device using an ultrasonic image has been put into practical use. In general, this kind of ultrasonic diagnostic device includes an ultrasonic probe with built-in ultrasonic transducers and a device body connected to the ultrasonic probe, and generates an ultrasonic image by transmitting an ultrasonic wave toward a subject from the ultrasonic probe, receiving an ultrasonic echo from the subject using the ultrasonic probe, and performing electrical processing on the reception signal in the device body.

When visualizing the needle inserted into the subject in an ultrasonic image, the needle that is inserted so as to be inclined at a predetermined angle with respect to the skin surface of the subject is inclined with respect to the ultrasonic wave transmitting and receiving surface of the ultrasonic probe, as shown in FIG. 16A. Accordingly, when transmitting the ultrasonic beam toward the target tissue from the transmission and reception opening, the specular reflection wave from the needle may deviate from the reception opening. In this case, it is known that a needle image cannot be visualized since the reception opening cannot receive the reflected wave from the needle. In addition, since the reflection at the needle tip is not a perfect specular reflection, a slight reflection returns to the reception opening. However, since the received signal strength is low, it is difficult to visualize the needle to the extent that the needle can be visually recognized.

In contrast, as shown in FIG. 16B, measures for receiving the reflected wave from the needle by tilting the ultrasonic beam so as to be perpendicular to the needle have been made.

However, since the visualization depth is limited by tilting the ultrasonic beam, it is not possible to draw either the needle tip or the target tissue even if it is possible to draw the needle. Accordingly, the positional relationship between the needle direction or the needle tip and the target tissue is not known.

JP2010-183935A focuses on the fact that the amount of high frequency components in the reflection signal from the needle tip portion is smaller than that in the reflection signal from portions other than the needle tip portion, and an ultrasonic image in which the position of the needle tip portion can be easily visually recognized is generated by capturing an image of the low frequency band and an image of the high frequency band, taking a difference therebetween, and superimposing the difference image on an image of another high frequency band.

In addition, JP2012-213606A improves the visibility of both the body tissue and the puncture needle in a displayed image by capturing reflected waves from the puncture needle by performing a plurality of scans while changing the transmission direction of the ultrasonic wave, generating ultrasonic images with improved visibility of the puncture needle, generating a needle image based on the plurality of ultrasonic images with the changed transmission directions and the normal tissue image, and combining the normal tissue image and the needle image.

SUMMARY OF THE INVENTION

In JP2010-183935A, however, the frequency difference between the reflection signal from the needle tip portion and reflection signals from portions other than the needle tip portion is small. Therefore, also in the portions other than the needle tip portion, the same frequency may be obtained due to isolated point-like reflection or reflection conditions. For this reason, it is difficult to visualize only the needle tip.

In addition, JP2012-213606A does not describe the visualization of the needle tip even though a plurality of needle images are generated by performing a scan in a plurality of directions.

It is an object of the present invention to provide an ultrasonic diagnostic device and an ultrasonic image generation method for specifying the position of the needle tip present in a deep portion of the subject and visualizing the needle tip in a tissue image in the ultrasonic diagnosis with the insertion of the needle into the subject.

In order to solve the aforementioned problem, the present invention provides an ultrasonic diagnostic device that transmits an ultrasonic wave toward a subject from an ultrasonic probe and generates an ultrasonic image based on obtained reception data. The ultrasonic diagnostic device includes: a tissue image generation unit that generates a tissue image of the subject by transmitting a transmission wave in a normal direction of an ultrasonic wave transmitting and receiving surface of the ultrasonic probe and receiving a reception wave from the normal direction of the subject; a needle information generation unit that generates needle information of a needle inserted into the subject by steering at least one of the transmission wave and the reception wave; a needle direction estimation unit that estimates a direction of the needle based on the needle information generated by the needle information generation unit; a search region setting unit that sets a search region of a needle tip in the tissue image based on the needle direction estimated by the needle direction estimation unit; a needle tip search unit that searches for the needle tip in the search region set by the search region setting unit; and a needle tip visualizing unit that visualizes the needle tip on the tissue image based on the needle tip found by the needle tip search unit.

Preferably, the needle information generation unit generates a plurality of pieces of the needle information with different steering directions by changing a steering direction to steer at least one of the transmission wave and the reception wave, and the needle direction estimation unit estimates the needle direction based on the plurality of pieces of needle information with different steering directions. It is preferable that the needle information generated by the needle information generation unit is needle image data.

The needle direction estimation unit can estimate the needle direction by Hough conversion.

It is preferable that the search region setting unit sets the search region that extends to both sides of the needle direction estimated by the needle direction estimation unit with a predetermined width.

It is preferable that the needle tip search unit searches for a point, at which a brightness value is a maximum, in the search region as the needle tip.

It is preferable that the needle tip search unit includes a needle tip pattern of the needle tip and searches for a point, at which a correlation with the needle tip pattern is a maximum, in the search region as the needle tip.

It is preferable that the needle tip visualizing unit visualizes a point image having a predetermined size at a position of the needle tip.

It is preferable that the needle tip visualizing unit visualizes a frame of a predetermined range from a position of the needle tip. The needle tip visualizing unit may change a brightness value or a color of the tissue image inside or outside the frame, or the needle tip visualizing unit may apply a translucent mask onto the tissue image inside or outside the frame.

When generating a series of a plurality of tissue images with movement of the needle tip, the needle tip search unit may compare a tissue image before movement of the needle tip with a tissue image after movement of the needle tip and search for the needle tip based on a change between the tissue images.

In addition, the present invention provides an ultrasonic image generation method of transmitting an ultrasonic wave toward a subject from an ultrasonic probe and generating an ultrasonic image based on obtained reception data. The ultrasonic image generation method includes: generating a tissue image of the subject by transmitting a transmission wave from the ultrasonic probe and receiving a reception wave from the subject; generating needle information of a needle inserted into the subject by steering at least one of the transmission wave and the reception wave; estimating a direction of the needle based on the needle information; setting a search region of a needle tip in the tissue image based on the estimated needle direction; searching for the needle tip in the set search region; and visualizing the needle tip on the tissue image based on the found needle tip.

According to the present invention, during the insertion, by specifying the position of the needle tip present in a deep portion of the subject and visualizing the needle tip in the tissue image, it is possible to visualize the positional relationship between the needle direction and the target tissue and the positional relationship between the needle tip and the target tissue in the tissue image.

BRIEF DESCRIPTION OF THE DRAWINGS

FIG. 1 is a block diagram showing the overall configuration of an ultrasonic diagnostic device according to an embodiment of the present invention.

FIG. 2 is a flowchart showing the operation of the ultrasonic diagnostic device shown in FIG. 1.

FIG. 3A is an explanatory view for explaining a scanning line V_i in a normal direction and a scanning line H_i in a steering direction in the ultrasonic diagnostic device shown in FIG. 1, FIG. 3B is an explanatory view of a tissue image corresponding to the scanning line V_i in the normal direction, and FIG. 3C is an explanatory view of a needle image corresponding to the scanning line H_i in the steering direction.

FIG. 4 is an example of a tissue image, which is generated by the ultrasonic diagnostic device shown in FIG. 1 and in which a needle direction L estimated from the needle image is visualized.

FIG. 5 is an example of a tissue image in which a search region F, which is set based on the needle direction L in the tissue image shown in FIG. 4, is visualized.

FIG. 6 is an enlarged extraction image of a region W shown in FIG. 5.

FIG. 7 is an example when a needle tip N, which is a point image in FIG. 6, is visualized.

FIG. 8 is an example when a needle tip N, a needle tip region NF, a needle body NB, and a search region F are visualized in the tissue image generated by the ultrasonic diagnostic device shown in FIG. 1.

FIG. 9 is an example when the brightness value inside or outside the needle tip region NF in the tissue image shown in FIG. 8 is changed.

DESCRIPTION OF THE PREFERRED EMBODIMENTS

Figures 10, 11:
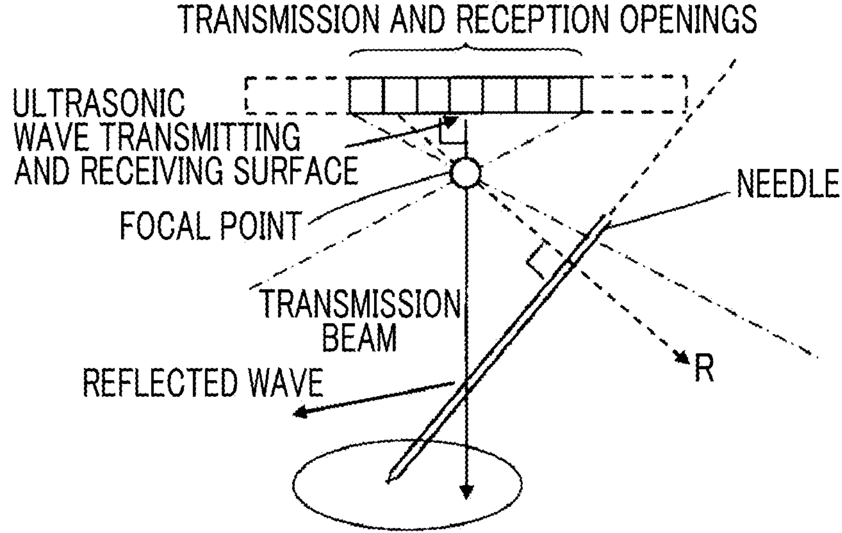
FIG. 10 is an example when a translucent mask is applied onto the inside or the outside of the needle tip region NF in the tissue image shown in FIG. 8.
FIG. 11 is an explanatory view when performing transmission focus processing in the normal direction and reception focus processing in the needle direction in the ultrasonic diagnostic device shown in FIG. 1.

Hereinafter, an ultrasonic diagnostic device and an ultrasonic image generation method according to the present invention will be described in detail with reference to the accompanying diagrams.

FIG. 1 is a block diagram showing the overall configuration of an ultrasonic diagnostic device according to an embodiment of the present invention.

The ultrasonic diagnostic device includes an ultrasonic probe 1, and a transmission circuit 2 and a reception circuit 3 are connected to the ultrasonic probe 1. A tissue image generation unit 4 and a needle image generation unit 5 are connected in parallel to the reception circuit 3. A needle tip visualizing unit 9 is connected to the tissue image generation unit 4, and a display unit 11 is connected to the needle tip visualizing unit 9 through a display control unit 10. A needle direction estimation unit 6 is connected to the needle image generation unit 5, a needle tip search unit 8 is connected to the needle direction estimation unit 6 through a search region setting unit 7, and the needle tip search unit 8 is connected to the needle tip visualizing unit 9. The search region setting unit 7 is connected to the tissue image generation unit 4.

A control unit 12 is connected to the transmission circuit 2, the reception circuit 3, the tissue image generation unit 4, the needle image generation unit 5, the needle tip visualizing unit 9, the needle direction estimation unit 6, the search region setting unit 7, the needle tip search unit 8, and the display control unit 10. An operation unit 13 and a storage unit 14 are connected to the control unit 12.

The tissue image generation unit 4 includes a phasing addition section 15A, a detection processing section 16A, a digital scan converter (DSC) 17A, and an image processing section 18A, which are connected sequentially from the reception circuit 3, and an image memory 19A connected to the DSC 17A.

Similarly, the needle image generation unit 5 includes a phasing addition section 15B, a detection processing section 16B, a digital scan converter (DSC) 17B, and an image processing section 18B, which are connected sequentially from the reception circuit 3, and an image memory 19B connected to the DSC 17B.

The ultrasonic probe 1 includes a plurality of elements arranged in a one-dimensional or two-dimensional array, and transmits an ultrasonic beam (transmission wave) based on a transmission signal supplied from the transmission circuit 2, receives an ultrasonic echo (reception wave) from the subject, and outputs a reception signal. For example, each element that forms the ultrasonic probe 1 is formed by a transducer in which electrodes are formed at both ends of the piezoelectric body formed of piezoelectric ceramic represented by lead zirconate titanate (PZT), a polymer piezoelectric element represented by polyvinylidene fluoride (PVDF), piezoelectric single crystal represented by lead magnesium niobate-lead titanate (PMN-PT), or the like.

When a pulsed or continuous-wave transmission signal voltage is applied to the electrodes of the transducer, the piezoelectric body expands and contracts to generate pulsed or continuous-wave ultrasonic waves from each transducer. By combination of these ultrasonic waves, an ultrasonic beam is formed. In addition, the respective transducers expand and contract by receiving the propagating ultrasonic waves, thereby generating electrical signals. These electrical signals are output as reception signals of the ultrasonic waves.

The transmission circuit 2 includes a plurality of pulsers, for example. The transmission circuit 2 performs transmission focus processing so that ultrasonic waves transmitted from the plurality of elements of the ultrasonic probe 1 form an ultrasonic beam based on the transmission delay pattern selected according to the control signal from the control unit 12, adjusts the amount of delay of each transmission signal, and supplies the adjusted signals to the plurality of elements. By adjusting the amount of delay of each transmission signal in the transmission circuit 2, the ultrasonic beam from the ultrasonic probe 1 can be steered at a predetermined angle with respect to the normal direction of the ultrasonic wave transmitting and receiving surface.

The reception circuit 3 performs amplification and A/D conversion of the analog reception signals output from the plurality of elements of the ultrasonic probe 1, and outputs digital reception signals to the phasing addition section 15A of the tissue image generation unit 4 or the phasing addition section 15B of the needle image generation unit 5 or to both of the phasing addition section 15A of the tissue image generation unit 4 and the phasing addition section 15B of the needle image generation unit 5 in response to the instruction from the control unit 12.

The phasing addition section 15A of the tissue image generation unit 4 acquires the digital reception signals from the reception circuit 3 in response to the instruction from the control unit 12, and performs reception focus processing by delaying the reception signals based on the reception delay pattern from the control unit 12 and adding the delayed reception signals. By the reception focus processing, reception data (sound ray signal) based on the ultrasonic echo from the target tissue is generated.

The detection processing section 16A generates a B-mode image signal, which is tomographic image information regarding a tissue within the subject, by correcting the attenuation due to the distance according to the depth of the reflection position of the ultrasonic wave and then performing envelope detection processing for the reception data.

The DSC 17A converts the B-mode image signal generated by the detection processing section 16A into an image signal according to the normal television signal scanning method (raster conversion). In addition, by converting the B-mode image signal in the DSC 17A, it is possible to grasp the positional relationship or the distance corresponding to the tissue of the actual subject on the B-mode image.

The image processing section 18A generates a B-mode image signal of the tissue image by performing various kinds of required image processing, such as gradation processing, on the B-mode image signal input from the DSC 17A.

The phasing addition section 15B of the needle image generation unit 5 acquires the digital reception signals from the reception circuit 3 in response to the instruction from the control unit 12, and performs reception focus processing by delaying the reception signals based on the reception delay pattern from the control unit 12 and adding the delayed reception signals. The phasing addition section 15B generates reception data (sound ray signal) based on the ultrasonic echo from the needle, which is steered at a predetermined angle with respect to the normal direction of the ultrasonic wave transmitting and receiving surface by adjusting the amount of delay of each reception signal.

Similar to the detection processing section 16A, the detection processing section 16B generates a B-mode image signal, which is tomographic image information regarding a tissue within the subject, by correcting the attenuation due to the distance according to the depth of the reflection position of the ultrasonic wave and then performing envelope detection processing for the reception data.

Similar to the DSC 17A, the DSC 17B converts the B-mode image signal generated by the detection processing section 16B into an image signal according to the normal television signal scanning method (raster conversion). In addition, by converting the B-mode image signal in the DSC 17B, it is possible to grasp the positional relationship or the distance corresponding to the tissue of the actual subject on the B-mode image.

The image processing section 18B generates a B-mode image signal of the needle image from the B-mode image signal input from the DSC 17B.

The needle direction estimation unit 6 estimates a needle direction, which indicates a direction in which the needle inserted into the subject is present, from the B-mode image signal of the needle image output from the image processing section 18B, and generates needle direction information indicating the position of the needle direction.

The search region setting unit 7 acquires the needle direction information from the needle direction estimation unit 6 and acquires the B-mode image signal of the tissue image from the image processing section 18A of the tissue image generation unit 4, visualizes a needle direction on the tissue image based on the needle direction information, and sets a search region for searching for the needle tip based on the needle direction on the tissue image. For example, a region that extends to both sides of the needle direction with a predetermined width may be set as a search region.

The needle tip search unit 8 generates the position information of the needle tip by searching for the needle tip in the search region, which is set by the search region setting unit 7, in the tissue image in which the needle direction and the search region are set.

The needle tip visualizing unit 9 acquires the position information of the needle tip from the needle tip search unit 8 and acquires the B-mode image signal of the tissue image from the image processing section 18A of the tissue image generation unit 4, and visualizes the needle tip on the tissue image.

Instead of visualizing the needle tip in the tissue image, for example, the needle tip visualizing unit 9 may visualize a needle direction from the needle tip to the base of the needle based on the needle direction information, or may visualize a search region based on the information of the search region.

The display control unit 10 acquires a B-mode image signal of the tissue image in which the needle tip is visualized by the needle tip visualizing unit 9, and displays the tissue image in which the needle tip is visualized on the display unit 11.

For example, the display unit 11 includes a display device, such as an LCD, and displays a tissue image, which is an ultrasonic image, under the control of the display control unit 10.

The control unit 12 controls each unit based on the instruction input from the operation unit by the operator. As described above, the control unit 12 selects and outputs a transmission delay pattern for the transmission circuit 2 or selects and outputs a reception delay pattern for the reception circuit 3, and outputs an instruction on phasing addition or the correction of attenuation and envelope detection processing, based on the reception delay pattern or the transmission delay pattern, to the phasing addition section 15A or the detection processing section 16A of the tissue image generation unit 4 or to the phasing addition section 15B or the detection processing section 16B of the needle image generation unit 5.

The operation unit 13 is used when the operator performs an input operation, and can be formed by a keyboard, a mouse, a trackball, a touch panel, and the like.

Various kinds of information input from the operation unit 13, information based on the above-described transmission delay pattern or reception delay pattern, information regarding the sound speed in an inspection target region of the subject, the focal position of the ultrasonic beam, and the transmission opening and the reception opening of the ultrasonic probe 1, an operation program required for the control of each unit, and the like are stored in the storage unit 14. Recording media, such as a hard disk, a flexible disk, an MO, an MT, a RAM, a CD-ROM, and a DVD-ROM, can be used as the storage unit 14.

Next, the operation of the ultrasonic diagnostic device according to an embodiment of the present invention to generate an ultrasonic image, in which a target tissue to be observed by the user is clearly imaged and the needle tip of the inserted needle is visualized, will be described.

Figure 2:
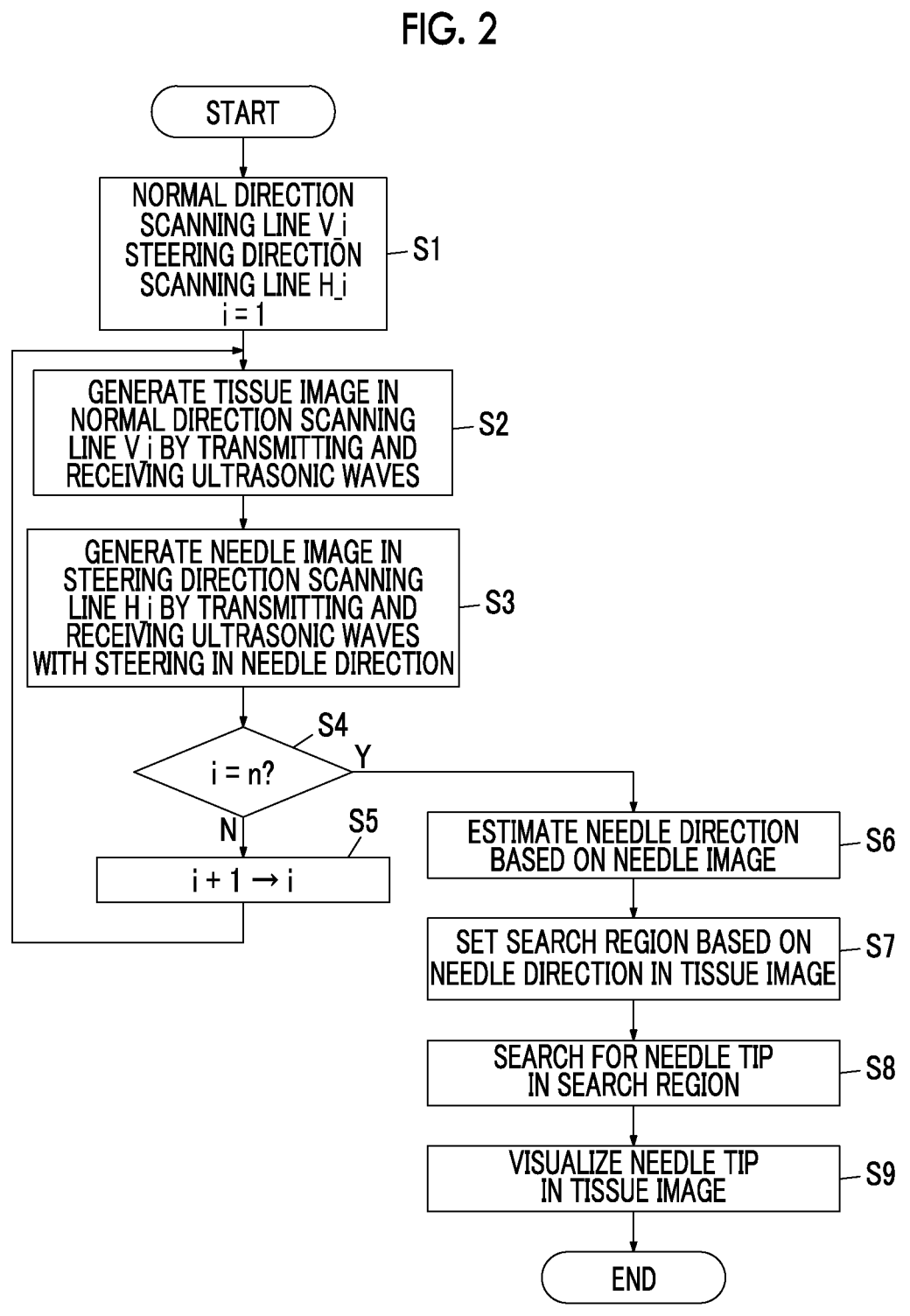

FIG. 2 is a flowchart showing the operation of an embodiment.

First, in step S1, i=1 is set in a scanning line V_i (i=1 to n) in a normal direction with respect to an ultrasonic wave transmitting and receiving surface S of the ultrasonic probe 1 and a scanning line H_i (i=1 to n) in a steering direction that is steered by a predetermined angle θ in the needle direction from the normal direction of the ultrasonic wave transmitting and receiving surface S, which are shown in FIG. 3A. Here, i is the order of the scanning line of the ultrasonic probe 1, and the ultrasonic probe 1 acquires a reception signal corresponding to each scanning line.

Then, in step S2, corresponding to the scanning line V_1 in the normal direction, the ultrasonic probe 1 acquires a reception signal corresponding to the scanning line V_1 in the normal direction by transmitting the ultrasonic beam toward the target tissue T in the normal direction of the ultrasonic wave transmitting and receiving surface S and receiving the ultrasonic echo from the normal direction of the ultrasonic wave transmitting and receiving surface S, and the tissue image generation unit 4 generates a tissue image corresponding to the normal direction scanning line V_1 shown in FIG. 3B and stores the tissue image in the image memory 19A.

Then, in step S3, corresponding to the scanning line H_1 in the steering direction, the ultrasonic probe 1 acquires a reception signal corresponding to the scanning line H_1 in the steering direction by transmitting the ultrasonic beam in the steering direction, which is steered by the predetermined angle θ toward the needle direction from the normal direction of the ultrasonic wave transmitting and receiving surface S, and receiving the ultrasonic echo from the steering direction, and the needle image generation unit 5 generates a needle image corresponding to the steering direction scanning line H_1 shown in FIG. 3C and stores the needle image in the image memory 19B. The predetermined angle θ may be a fixed value set in advance, or may be acquired from a device (not shown) for calculating the angle formed by the normal direction and the insertion angle of the probe. Alternatively, a direction in which a strong signal is returned after transmitting and receiving signals in a plurality of directions in advance may be set as the predetermined angle.

Thus, when a B-mode image signal of the tissue image corresponding to the first normal direction scanning line V_1 and a B-mode image signal of the needle image corresponding to the first steering direction scanning line H_1 are stored in the image memories 19A and 19B, respectively, it is determined whether or not i=n, that is, it is determined whether or not B-mode image signals of the tissue image and the needle image have been generated in all scanning lines of the ultrasonic probe 1 in step S4.

In this case, since the value of i is still 1, the process proceeds to step S5 to increase i by 1, that is, to move to the second scanning line, and steps S2 to S4 are repeated to generate B-mode image signals of the corresponding tissue image and needle image. Similarly, until i=n, the value of i is increased by 1 in a sequential manner, and steps S2 and S3 are repeated.

In this manner, when B-mode image signals of tissue images for all of the "n" scanning lines V_1 to V_n and B-mode image signals of needle images for all of the "n" scanning lines H_1 to H_n are generated, the process proceeds to step S6 from step S4.

In step S6, the needle direction estimation unit 6 estimates a needle direction L based on the B-mode image signal obtained by performing image processing by scan-converting the needle image stored in the image memory 19B. For example, the needle direction is performed by calculating the brightness distribution in the entire needle image or in a predetermined region in which it is assumed that a needle is included, detecting a straight line in the entire needle image or in the predetermined region by Hough conversion and setting it as a needle direction, and setting the position information of the needle direction as needle direction information. When a straight line is detected by Hough conversion, a brightness value may be multiplied as a weighting factor when converting each pixel to the curve in the Θρ coordinate system and superimposing the curves on each other. Through this method, a high-brightness straight line, such as a needle, can be easily detected. The needle direction information of the needle direction L estimated by the needle direction estimation unit 6 is output to the search region setting unit 7.

Figures 4, 5:
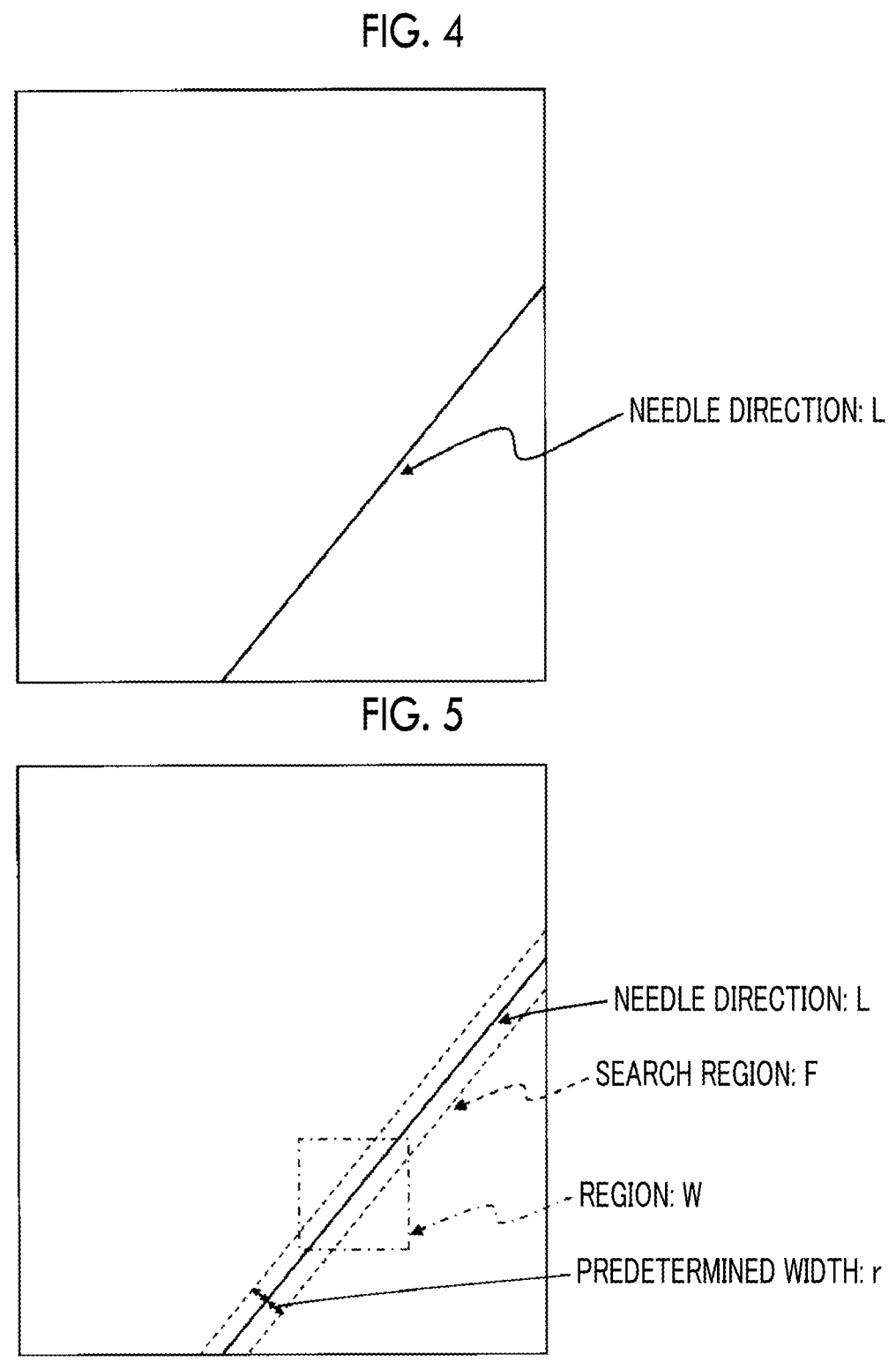

In step S7, the search region setting unit 7 superimposes a signal in the needle direction L on the B-mode image signal, which is obtained by performing image processing by scan-converting the tissue image stored in the image memory 19B, based on the needle direction information output from the needle direction estimation unit 6 as shown in FIG. 4, and sets a search region F extending from the needle direction L of the tissue image to both sides of the needle direction L with a predetermined width r as shown in FIG. 5. The B-mode image signal of the tissue image in which the needle direction L and the search region F are set is output to the needle tip search unit 8. For example, the predetermined width r may be set to three to five times the width of the needle based on the width of the needle inserted into the body.

Figures 6, 7:
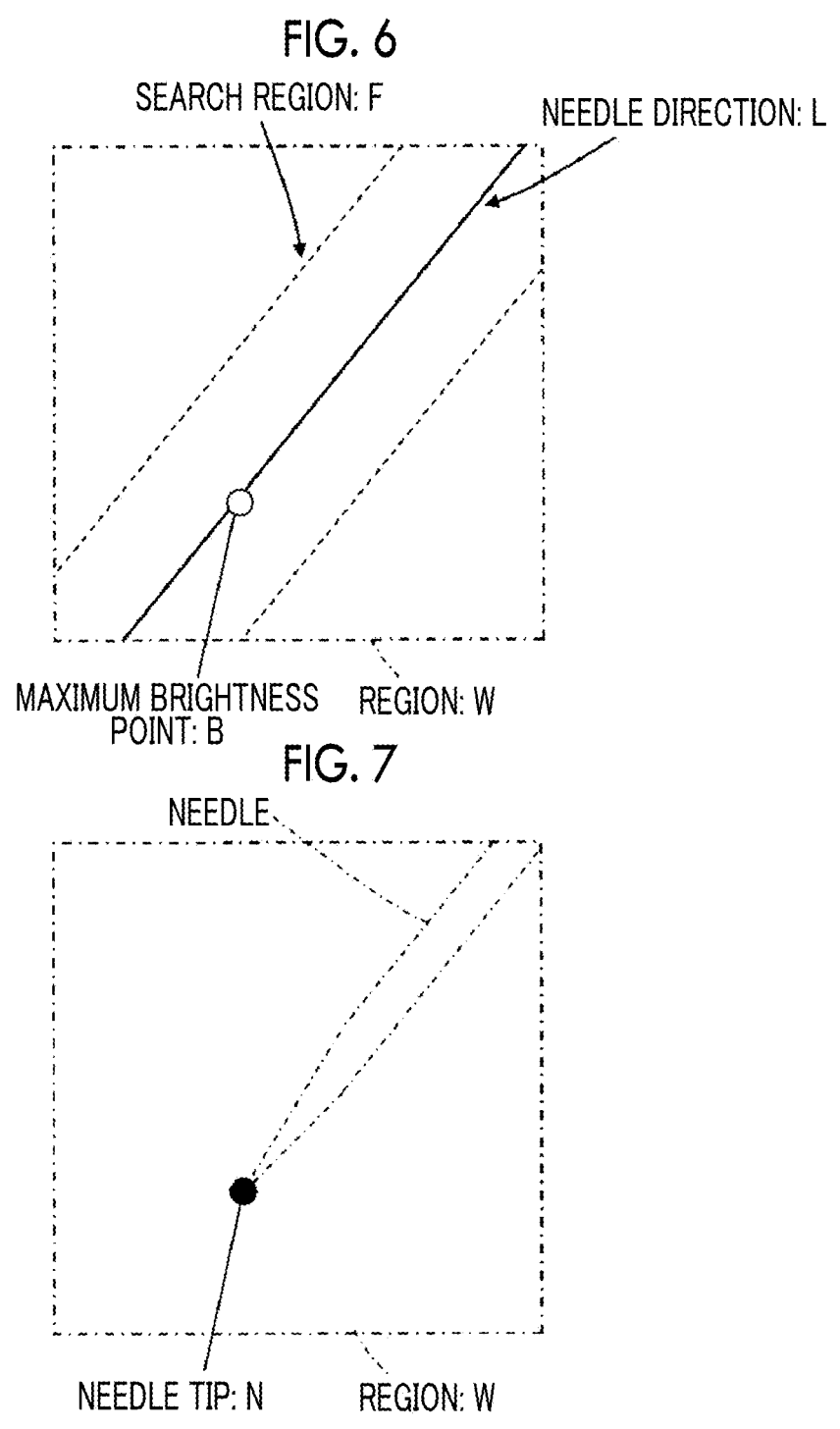

In step S8, the needle tip search unit 8 calculates the brightness distribution of the tissue image, and determines a maximum brightness point B in a search region F as a needle tip as shown in FIG. 6 obtained by extracting a region W in FIG. 5 in an enlarged manner. Alternatively, the needle tip search unit 8 may have a needle tip pattern, such as an image of the needle tip, in advance, take a correlation with the needle tip pattern in the tissue image in the search region F, and determine a point at which the correlation is the maximum as the needle tip. The position information of the needle tip found by the needle tip search unit 8 is output to the needle tip visualizing unit 9. In addition, the needle tip search unit 8 may output needle direction information or the information of the search region together with the position information of the needle tip.

In step S9, as shown in FIG. 7, the needle tip visualizing unit 9 visualizes a needle tip N, which is a point image having a predetermined size, in the tissue image from the position information of the needle tip found by the needle tip search unit 8. The B-mode image signal of the tissue image in which the needle tip is visualized is output to the display control unit 10, and is displayed as a tissue image in which the needle tip is visualized on the display unit 11.

By visualizing the needle tip N in the tissue image, it is possible to clearly grasp the positional relationship between the needle tip and the target tissue in the tissue image.

Not only does the needle tip visualizing unit 9 visualize the needle tip N in the tissue image, but also it is possible to adopt various kinds of display methods for making the needle tip clear in the tissue image. For example, as shown in FIG. 8, a circular frame showing a needle tip region NF that extends by a predetermined radius from the position of the needle tip may be displayed, or the search region F may be displayed based on the information of the above-described search region, or a needle body NB, which is obtained by visualizing the needle direction L from the needle tip N or which is obtained by connecting the needle tip N to the base portion of the needle direction L in a straight line may be visualized based on the needle direction L.

The needle tip visualizing unit 9 may change the brightness value or the color of a tissue image inside or outside the needle tip region NF surrounded by the circular frame as shown in FIG. 9, or may apply a translucent mask onto the tissue image of the inside or the outside of the needle tip region NF surrounded by the circular frame as shown in FIG. 10.

Instead of the circular frame described above, a frame having a predetermined shape, for example, a rectangular frame or a rhombic frame having a position of the needle tip on its center, may be displayed.

By emphasizing the needle tip by visualizing the needle tip in the tissue image as described above, the needle tip can be easily visually recognized in the tissue image. Therefore, it is possible to clearly grasp the positional relationship between the needle direction and the target tissue and the positional relationship between the needle tip and the target tissue.

Modification Example 1

In the ultrasonic diagnostic device according to the embodiment described above, when generating a needle image, transmission focus processing is performed by steering the ultrasonic beam by a predetermined angle in the needle direction and reception focus processing is performed by steering the ultrasonic echo by the predetermined angle θ in the needle direction, thereby generating a needle image. For example, as shown in FIG. 11, a tissue image can be generated by performing transmission focus processing on the ultrasonic wave toward a predetermined focal point in the normal direction of the ultrasonic wave receiving surface and performing reception focus processing on the ultrasonic echo from the target tissue in the normal direction of the ultrasonic wave transmitting and receiving surface, and a needle image can be generated by performing reception focus processing on the ultrasonic echo from the needle in the R direction indicated by the dotted arrow.

According to the reception focus processing in the modification example 1, in addition to the effect of the embodiment described above, it is possible to improve the refresh rate of the displayed image since the tissue image and the needle image can be generated at the same time by one transmission of the ultrasonic wave.

Modification Example 2

In the ultrasonic diagnostic device according to the embodiment described above, the needle direction is estimated based on one needle image. However, for example, a plurality of needle images with different steering directions may be generated by changing the steering direction for steering at least one of the direction of transmission focus processing, which is the transmission direction of the ultrasonic beam, and the direction of reception focus processing of the ultrasonic echo, the sharpest needle image among the plurality of needle images may be selected, and the above-described needle direction may be estimated based on the selected sharpest needle image.

Figures 12, 13, 14:
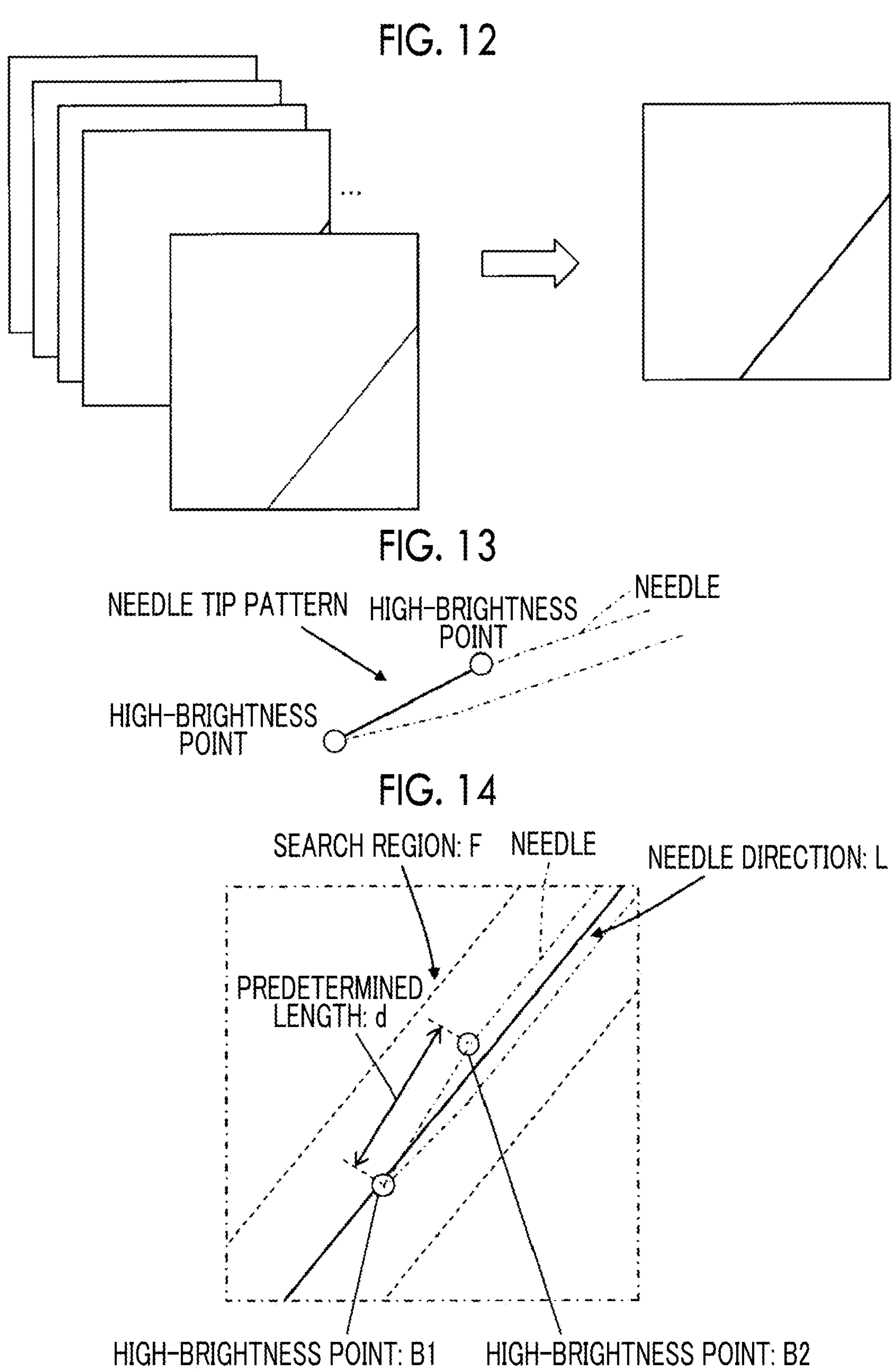
FIG. 12 is an explanatory view when selecting a needle image for estimating the needle direction from a plurality of needle images with different steering directions.
FIG. 13 is a schematic diagram showing an example of the needle tip pattern.
FIG. 14 is an explanatory view when searching for the needle tip based on the needle tip pattern.

The needle direction estimation unit 6 acquires a plurality of needle images with different steering directions from the needle image generation unit 5, and selects a needle image in which the needle is visualized best as shown in FIG. 12. For the selection of a needle image in which the needle is visualized best, the brightness distribution in the entire needle image or a predetermined region in which it is assumed that a needle is included may be calculated for each needle image, and a needle image including a point of the highest brightness value may be selected or a needle image having a maximum average brightness value may be selected, for example. As described above, it is possible to estimate the needle direction by selecting a needle image in which the needle is visualized best. That is, a direction perpendicular to the steering direction in which the needle is visualized best can be estimated to be the needle direction.

In addition, for example, the brightness distribution in the entire needle image or a predetermined region in which it is assumed that a needle is included may be calculated for a plurality of needle images with different steering directions, a straight line may be detected by the Hough conversion or the like, and a needle image in which the average brightness value of the straight line is the maximum may be selected. Alternatively, a needle image having a point of the maximum brightness value on the straight line, which is higher than points of the maximum brightness values on the straight lines in the other needle images, may also be selected.

The predetermined region in which it is assumed that a needle is included is assumed from the approximate angle of the insertion, for example.

The needle direction estimation unit 6 estimates the needle direction based on the selected needle image. Alternatively, the needle direction estimation unit 6 may calculate the brightness distribution in the entire needle image or a predetermined region in which it is assumed that a needle is included using all of a plurality of needle images with different steering directions, detect a straight line based on the brightness distribution in the entire needle image or the predetermined region by the Hough conversion or the like, and set the straight line as a needle direction.

Modification Example 3

In the ultrasonic diagnostic device according to the embodiment described above, as shown in FIGS. 6 and 7, the needle tip search unit 8 determines the maximum brightness point B in the search region F as a needle tip. However, the needle tip search unit 8 may have a needle tip pattern in advance and search for the needle tip based on the needle tip pattern. As a needle tip pattern, for example, as shown in FIG. 13, there is an image that is a line segment, which connects the needle tip and the end of the cut surface of the needle to each other and has a predetermined length d, and that has a high-brightness point at both ends of the line segment.

A portion in which the reflection angle is changed, such as the tip of the needle or the end of the cut surface of the needle, tends to have high brightness in a tissue image. Therefore, for example, the needle tip search unit 8 may have the above-described needle tip pattern. Then, as shown in FIG. 14, the needle tip search unit 8 may search for a high-brightness point B1 and a high-brightness point B2, which are considered to be the most correlated with the needle tip pattern in the search region F, and determine the high-brightness point B1 located in a deep portion of the subject, between the high-brightness point B1 and the high-brightness point B2, as a needle tip.

Modification Example 4

In the ultrasonic diagnostic device according to the embodiment described above, when the needle moves in the subject, when capturing a plurality of tissue images at least before and after the movement or when capturing tissue images of a plurality of frames as a moving image with the movement of the needle, the needle tip search unit 8 may search for the needle tip by comparing the tissue image before the movement with the tissue image after the movement.

Figures 15A, 15B:
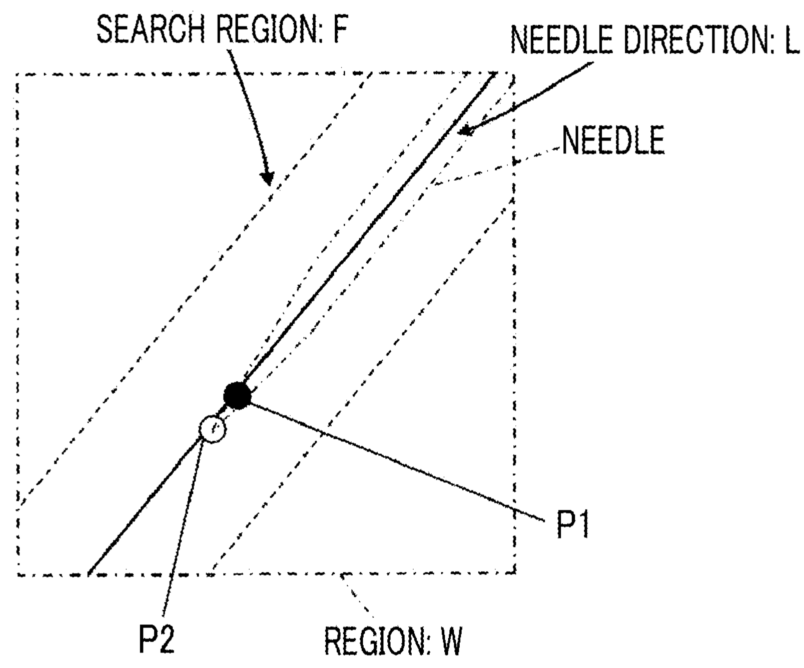
FIG. 15A is an example of a tissue image captured before the movement of the needle tip when capturing a plurality of tissue images with the movement of the needle tip.
FIG. 15B is an example of a tissue image captured after the movement of the needle tip.
Figure 16A:
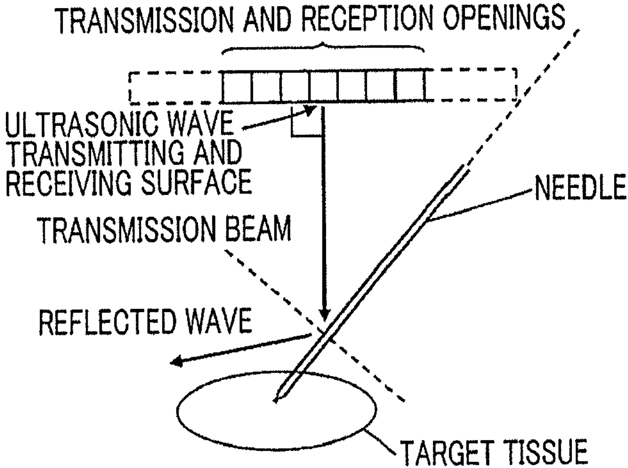
FIG. 16A is a diagram showing that the specular reflection of a needle by the ultrasonic beam in the normal direction deviates from the reception opening in the subject into which the needle is inserted.
Figure 16B:
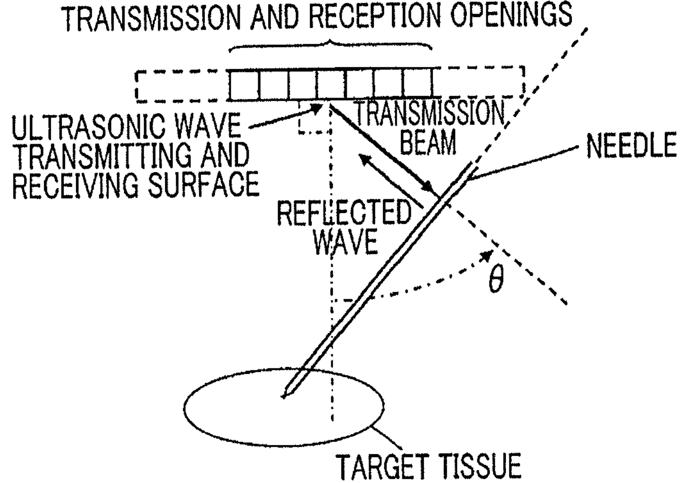
FIG. 16B is a diagram showing that an ultrasonic echo based on reflection from the needle can be received by transmitting the ultrasonic beam in a state in which the ultrasonic beam is steered in the needle direction in the subject into which the needle is inserted.

For example, the needle tip search unit 8 may calculate the brightness distribution in each of the tissue image before movement and the tissue image after movement and search for the needle tip based on the change in the brightness value. By comparing FIG. 15A that is a tissue image before movement with FIG. 15B that is a tissue image after movement, a point P2 where the brightness value becomes suddenly large in FIG. 15B may be determined as the needle tip, or a point P1 where the brightness value becomes suddenly small may be determined as the needle tip. In addition, the point P2 may be determined as the needle tip based on the fact that the point P2 where the brightness value becomes suddenly large and the point P1 where the brightness value becomes suddenly small are adjacent to each other. A needle tip pattern image of the brightness change including the point P2 where the brightness value becomes suddenly large and the point P1 where the brightness value becomes suddenly small may be prepared in advance, and a point considered to be the most correlated with the needle tip pattern in the search region F in the image of the brightness change between the tissue image before movement and the tissue image after movement may be searched for and determined to be the needle tip.

Instead of the brightness value change described above, for example, the needle tip search unit 8 may compare the tissue image before movement with the tissue image after movement, calculate the amount of movement and the movement direction between the images at each point in a predetermined region including the needle tip by the two-dimensional correlation operation or the like, and determine a point of the largest amount of movement or a point of the largest spatial change in the amount of movement or the movement direction as the needle tip.

For example, the needle tip search unit 8 may compare the tissue image before movement with the tissue image after movement, calculate a change before and after movement in the image pattern near each point in a predetermined region including the needle tip by the two-dimensional correlation operation or the like, and determine a point of the largest image pattern change or a point of the largest spatial change of the image pattern change as the needle tip.

Modification Example 5

In the ultrasonic diagnostic device according to the embodiment described above, the needle image generation unit 5 generates a needle image, and the needle direction estimation unit 6 estimates a needle direction based on the needle image. However, it is possible to estimate a needle direction even if a needle image is not generated. For example, the needle direction may be estimated based on the reception signal from each element of the ultrasonic probe 1, and the needle direction may be estimated based on the reception data (sound ray signal) after phasing addition.

Also in the modification examples 2 to 5, it is possible to visualize the needle tip in the tissue image as in the embodiment described above. Therefore, since the needle tip can be easily visually recognized in the tissue image, it is possible to clearly grasp the positional relationship between the needle direction and the target tissue and the positional relationship between the needle tip and the target tissue.

While the ultrasonic diagnostic device and the ultrasonic image generation method of the present invention have been described in detail, the present invention is not limited to the embodiments described above, and various modifications or changes may be made without departing from the scope and spirit of the present invention.

EXPLANATION OF REFERENCES

1: ultrasonic probe
2: transmission circuit
3: reception circuit
4: tissue image generation unit
5: needle image generation unit
6: needle direction estimation unit
7: search region setting unit
8: needle tip search unit
9: needle tip visualizing unit
10: display control unit
11: display unit
12: control unit
13: operation unit
14: storage unit
15A, 15B: phasing addition section
16A, 16B: detection processing section
17A, 17B: DSC
18A, 18B: image processing section
19A, 19B: image memory
V_i: normal direction scanning line
H_i: steering direction scanning line
L: needle direction
r: predetermined width
F: search region
W: region
B: maximum brightness point
N: needle tip
NF: needle tip region
NB: needle body
d: predetermined length
B1, B2: high-brightness point
θ: steering angle

What is claimed is:

1. A control method of an ultrasound diagnostic apparatus, wherein the ultrasound diagnostic apparatus comprises: an ultrasonic probe including a plurality of elements; and one or more processors, the method comprising:

transmitting, from the plurality of elements of the ultrasonic probe toward a target tissue of a subject into which a needle is inserted, a plurality of ultrasonic waves by one transmission, wherein transmission focus processing has been performed on the plurality of ultrasonic waves transmitted from the plurality of elements by the one transmission such that the plurality of ultrasonic waves are transmitted toward one focal point in a normal direction of an ultrasonic wave transmitting and receiving surface of the plurality of elements of the ultrasonic probe;

generating a plurality of pieces of reception data by receiving, by the plurality of elements, a plurality of reception waves which are reflected by the target tissue resulting from the plurality of ultrasonic waves, respectively;

performing a first reception focus processing on the plurality of pieces of reception data along the normal direction of the ultrasonic wave transmitting and receiving surface, to generate a plurality of pieces of processed first reception data, respectively;

generating a tissue image of the subject based on the plurality of pieces of processed first reception data;

performing a second reception focus processing on the plurality of pieces of reception data along a first steering direction to generate a plurality of pieces of processed second reception data, respectively, wherein the first steering direction (i) extends in a direction steered from the normal direction of the ultrasonic wave transmitting and receiving surface and (ii) includes a direction that is a right angle with respect to a direction in which the needle extends; generating at least one needle image of the needle based on the plurality of pieces of processed second reception data, respectively;

generating a needle direction of the needle based on the at least one generated needle image; and superimposing the generated needle direction on the tissue image.

2. The control method according to claim 1, further comprising:

setting a search region for searching for a needle tip of the needle on the tissue image based on the needle direction on the tissue image;

searching for the needle tip in the set search region; and visualizing the needle tip on the tissue image based on the found needle tip.

3. The control method according to claim 1, wherein the needle direction is generated by Hough conversion.

4. The control method according to claim 2, wherein the search region that extends to both sides of the needle direction with a predetermined width is set.

5. The control method according to claim 2, wherein a point, at which a brightness value is a maximum, in the search region is searched as the needle tip.

6. The control method according to claim 2, wherein a needle tip pattern of the needle tip is included, and a point, at which a correlation with the needle tip pattern is a maximum, in the search region is searched as the needle tip.

7. The control method according to claim 2, wherein a point image having a predetermined size at a position of the needle tip is visualized.

8. The control method according to claim 2, wherein a frame of a predetermined range from a position of the needle tip is visualized.

9. The control method according to claim 8, wherein a brightness value or a color of the tissue image inside or outside the frame is changed.

10. The control method according to claim 8, wherein a translucent mask is applied onto the tissue image inside or outside the frame.

11. The control method according to claim 2, wherein, when generating a series of a plurality of tissue images with movement of the needle tip, a tissue image before movement of the needle tip is compared with a tissue image after movement of the needle tip, and the needle tip is searched for based on a change between the tissue images.

12. The control method according to claim 2, wherein the searching for the needle tip performs at least one of having a needle tip pattern comprising an image of the needle tip, taking a correlation with the needle tip pattern in the tissue image in the search region, and determining a point where correlation is the maximum, or a high-brightness point which is the most correlated with the needle tip pattern as the needle tip, capturing the tissue images before and after movement of the needle which moves in the subject, calculating the brightness distribution in each of the tissue image before movement and the tissue image after movement and determining a point where a brightness value becomes suddenly large, a point where the brightness value becomes suddenly small, or a point where is the most correlated with the needle tip pattern in the search region in an image of the brightness change between the tissue image before movement and the tissue image after movement as the needle tip, comparing the tissue image before movement with the tissue image after movement, calculating an amount of movement and a movement direction between both images at each point in the search region including the needle tip by a two-dimensional correlation operation, and determining a point of the largest amount of movement, a point of the largest spatial change in the amount of movement, or a point of the largest spatial change in the movement direction as the needle tip, and comparing the tissue image before movement with the tissue image after movement, calculating a change before and after movement in an image pattern at each point in the search region including the needle tip by the two-dimensional correlation operation, and determining a point of the largest image pattern change or a point of the largest spatial change of the image pattern change as the needle tip, and generates position information of the needle tip.

13. The control method according to claim 2, wherein the searching for the needle tip performs calculating brightness distribution of the search region in the tissue image, and determining a maximum brightness point in the search region as the needle tip.

14. A non-transitory computer readable recording medium having recorded thereon a program for causing a computer to execute each step of the control method according to claim 1.

15. The non-transitory computer readable recording medium according to claim 14, wherein the searching for the needle tip performs at least one of having a needle tip pattern comprising an image of the needle tip, taking a correlation with the needle tip pattern in the tissue image in the search region, and determining a point where correlation is the maximum, or a high-brightness point which is the most correlated with the needle tip pattern as the needle tip, capturing the tissue images before and after movement of the needle which moves in the subject, calculating the brightness distribution in each of the tissue image before movement and the tissue image after movement and determining a point where a brightness value becomes suddenly large, a point where the brightness value becomes suddenly small, or a point where is the most correlated with the needle tip pattern in the search region in an image of the brightness change between the tissue image before movement and the tissue image after movement as the needle tip, comparing the tissue image before movement with the tissue image after movement, calculating an amount of movement and a movement direction between both images at each point in the search region including the needle tip by a two-dimensional correlation operation, and determining a point of the largest amount of movement, a point of the largest spatial change in the amount of movement, or a point of the largest spatial change in the movement direction as the needle tip, and comparing the tissue image before movement with the tissue image after movement, calculating a change before and after movement in an image pattern at each point in the search region including the needle tip by the two-dimensional correlation operation, and determining a point of the largest image pattern change or a point of the largest spatial change of the image pattern change as the needle tip, and generates position information of the needle tip.

16. The non-transitory computer readable recording medium according to claim 14, wherein the searching for the needle tip performs calculating brightness distribution of the search region in the tissue image, and determining a maximum brightness point in the search region as the needle tip.

* * * * *